US012664783B2

(12) United States Patent
Murali et al.

(10) Patent No.: US 12,664,783 B2
(45) Date of Patent: Jun. 23, 2026

(54) BED OCCUPANCY DETECTION USING GEOMETRIC FEATURES FROM POINT CLOUDS

(71) Applicant: Verb Surgical Inc., Santa Clara, CA (US)

(72) Inventors: Ashwath Narayan Murali, Munich (DE); Yiming Xu, Sunnyvale, CA (US); Juri Platonov, Munich (DE)

(73) Assignee: Auris Health, Inc., Santa Clara, CA (US)

( * ) Notice: Subject to any disclaimer, the term of this patent is extended or adjusted under 35 U.S.C. 154(b) by 511 days.

(21) Appl. No.: 18/170,431

(22) Filed: Feb. 16, 2023

(65) Prior Publication Data

US 2024/0282112 A1     Aug. 22, 2024

(51) Int. Cl.
*G06V 20/52* (2022.01)
*G06V 10/26* (2022.01)
(Continued)

(52) U.S. Cl.
CPC .............. *G06V 20/52* (2022.01); *G06V 10/26* (2022.01); *G06V 10/467* (2022.01);
(Continued)

(58) Field of Classification Search
CPC .... G06V 10/26; G06V 10/467; G06V 10/774; G06V 20/52; G06V 20/64; G06H 40/20; G06H 40/67; G06T 7/73; G06T 17/00
See application file for complete search history.

(56) References Cited

U.S. PATENT DOCUMENTS 10,395,123 B2     8/2019 Franz et al.
10,475,206 B1 *   11/2019 Rush ....................... G06T 7/254
(Continued)

FOREIGN PATENT DOCUMENTS

CN          111127550 A  *  5/2020  ............... G06T 7/11
CN          113219439 A  *  8/2021  ............. G01S 17/89

OTHER PUBLICATIONS

Bauer et al. "Modeling bed exit likelihood in a camera-based automated video monitoring application," 2017 IEEE Interntl. Conf. on Electro Info. Tech. (EIT), Lincoln, NE, USA, 2017, pp. 056-061. Accessed May 22, 2025 via <https://ieeexplore.ieee.org/document/8053330> (Year: 2017).*

(Continued)

*Primary Examiner* — John Villecco
*Assistant Examiner* — Joshua B. Crockett
(74) *Attorney, Agent, or Firm* — Aikin & Gallant, LLP

(57) ABSTRACT

Embodiments described herein provide systems and techniques for detecting hospital bed occupancy based on three-dimensional (3D) point clouds of the hospital bed extracted from depth images. In one aspect, a process for determining if a bed inside an operating room (OR) is occupied by a patient is disclosed. This process begins by receiving a 3D point cloud of a bed object within a depth image captured inside the OR. The process then segments the 3D point cloud of the bed object into a plurality of segments in both a length direction and a width direction of the bed object. Next, the process extracts a set of geometric features from the plurality of segments. The process subsequently applies a binary classifier to the set of geometric features to classify the bed object as either being occupied by a patient or not being occupied by a patient.

23 Claims, 10 Drawing Sheets

HOSPITAL-BED OCCUPANCY DETECTION SYSTEM 100

(51) Int. Cl.

| | |
|---|---|
| *G06V 10/46* | (2022.01) |
| *G06V 10/774* | (2022.01) |
| *G16H 40/20* | (2018.01) |
| *G16H 40/67* | (2018.01) |

(52) U.S. Cl.
CPC ........... *G06V 10/774* (2022.01); *G16H 40/20* (2018.01); *G16H 40/67* (2018.01)

(56) References Cited

U.S. PATENT DOCUMENTS

| | | | | |
|---|---|---|---|---|
| 10,535,146 | B1 | 1/2020 | Buibas et al. | |
| 2013/0289432 | A1* | 10/2013 | Van Vugt | A61B 5/0077 |
| | | | | 600/534 |
| 2016/0125620 | A1* | 5/2016 | Heinrich | A61B 5/1113 |
| | | | | 382/103 |
| 2016/0267327 | A1 | 9/2016 | Franz et al. | |
| 2020/0265602 | A1* | 8/2020 | Ostadabbas | G06V 40/103 |
| 2021/0195120 | A1 | 6/2021 | King | |
| 2021/0256705 | A1 | 8/2021 | Yu et al. | |
| 2021/0278857 | A1* | 9/2021 | Wei | G05D 1/0238 |
| 2022/0080060 | A1 | 3/2022 | Jarvis | |
| 2022/0189119 | A1 | 6/2022 | Seo | |

| | | | |
|---|---|---|---|
| 2023/0306629 | A1 | 9/2023 | Cho et al. |
| 2023/0360322 | A1 | 11/2023 | Majewski et al. |
| 2023/0368492 | A1 | 11/2023 | Xu et al. |

OTHER PUBLICATIONS

Camera Calibration with OpenCV, OpenCV, retrieved from the Internet on May 11, 2022, <https://docs.opencv.org/2.4/doc/tutorials/calib3d/camera_calibration/camera_calibration.html>, 11 pages.

Non-Final Office Action received for U.S. Appl. No. 17/741,812, mailed on Nov. 21, 2024, 28 pages.

Extended European Search Report and Search Opinion received for EP Application No. 24157832.7, mailed on Jun. 24, 2024, 9 pages.

Grimm, T., et al., "Sleep position classification from a depth camera using Bed Aligned Maps", 2016 23rd International Conference on Pattern Recognition (ICPR), Dec. 4, 2016, pp. 319-324.

Martinez, M., et al., "BAM!" Depth-Based Body Analysis in Criti, Sat 2015 18th International Conference, 2015, pp. 465-472.

Mecocci, A., et al., "Range Image Processing for Real Time Hospital-Room Monitoring", Lecture Notes in Computer Science, vol. 9475, Jan. 1, 2015, pp. 81-92.

Notice of Allowance received for U.S. Appl. No. 17/741,812, mailed May 20, 2025, 9 pages.

European Examinarion Report received for EP Patent Application No. 24157832.7, mailed Dec. 19, 2025, 8 pages total.

\* cited by examiner

HOSPITAL-BED OCCUPANCY DETECTION SYSTEM 100

POINT CLOUD 202 WITH X-SEGMENTATION

POINT CLOUD 202 WITH Y-SEGMENTATION

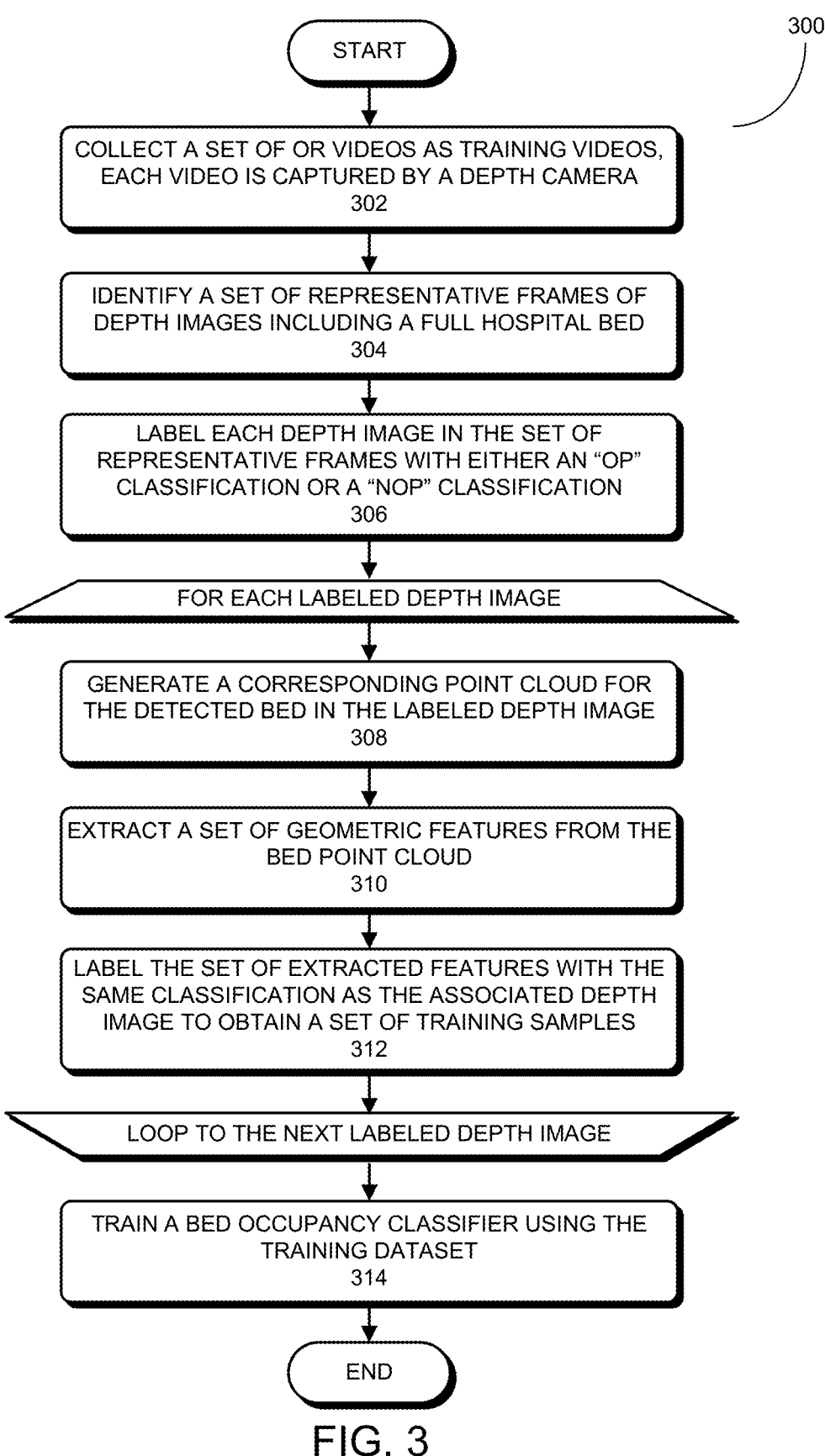

300

START

COLLECT A SET OF OR VIDEOS AS TRAINING VIDEOS,
EACH VIDEO IS CAPTURED BY A DEPTH CAMERA
302

IDENTIFY A SET OF REPRESENTATIVE FRAMES OF
DEPTH IMAGES INCLUDING A FULL HOSPITAL BED
304

LABEL EACH DEPTH IMAGE IN THE SET OF
REPRESENTATIVE FRAMES WITH EITHER AN "OP"
CLASSIFICATION OR A "NOP" CLASSIFICATION
306

FOR EACH LABELED DEPTH IMAGE

GENERATE A CORRESPONDING POINT CLOUD FOR
THE DETECTED BED IN THE LABELED DEPTH IMAGE
308

EXTRACT A SET OF GEOMETRIC FEATURES FROM THE
BED POINT CLOUD
310

LABEL THE SET OF EXTRACTED FEATURES WITH THE
SAME CLASSIFICATION AS THE ASSOCIATED DEPTH
IMAGE TO OBTAIN A SET OF TRAINING SAMPLES
312

LOOP TO THE NEXT LABELED DEPTH IMAGE

TRAIN A BED OCCUPANCY CLASSIFIER USING THE
TRAINING DATASET
314

END

FIG. 3

FROM
DT400-2

DT400-3

BED OCCUPANCY DETECTION USING GEOMETRIC FEATURES FROM POINT CLOUDS

TECHNICAL FIELD

The disclosed embodiments generally relate to computer-vision and deep-learning techniques for improving operating room (OR) workflow efficiencies. More specifically, the disclosed embodiments relate to detecting whether or not a hospital bed in the OR is occupied by a patient using depth images without any RGB/color information.

BACKGROUND

Operating room (OR) costs are among one of the highest medical and healthcare-related costs in the US. With sky-rocketing healthcare expenditures, OR-costs management aimed at reducing OR costs and increasing OR efficiency has become an increasingly important research subject. One sure way to improve OR efficiency is to optimize the utilization of OR resources. Many hospitals manage multiple operating rooms at the same time and have hospital staff fill various roles on an ever-changing schedule due to various factors. To achieve efficient resource allocation and staff assignment, it is important to maintain a robust system for communication and coordination. Majority of the OR responsibilities are taken by circulating nurses, who not only need to prepare for surgical tools and materials and to monitor and escort the patients, but also keep track of the OR schedules and workflows. However, hospitals are also increasingly exploring digital solutions that use sensors/camera systems to facilitate and automate tracking and scheduling OR workflows.

One of the higher priorities in the OR workflow tracking and scheduling is to track where the patient is located during a surgical procedure, especially when the patient is on a hospital bed being pushing into or out of the OR. The ability to detect a patient/human on the hospital bed entering or exiting the OR can be used to trigger an OR status indicating whether the hospital bed is being occupied or not, and/or whether the OR team needs to be ready for surgery or not.

Existing techniques for detecting the presence of an object or a person in OR video streams are generally based on RGB/color images. When RGB images are used, detecting the presence of a person is based on using face detection models and extracting face features. However, using RGB images in the OR is subject to privacy rules and concerns, and therefore would need user consent because the captured images could include personal identifiable information (PII). In addition to requiring the patient's consent, the PII needs to be removed from the RGB images before they can be used, which inevitably add to the cost and complexity of RGB-image solutions. There are also existing efforts for detecting human poses based on two-dimensional (2D) images without the above RGB information. Unfortunately, such techniques suffer from the drawbacks that if a patient is covered under a blanket/bed sheet or occluded by nurses/surgeons, the corresponding detectors would fail.

Hence, what is needed is a sensor-based OR workflow tracking technique that can detect whether a hospital bed in the OR is occupied by a patient or not without the drawbacks of the existing techniques.

SUMMARY

Disclosed are various operating room (OR) bed occupancy detection systems and techniques based on three-dimensional (3D) point clouds of the hospital beds/surgical tables extracted from depth images of the OR captured by one or more depth cameras installed in the OR. Specifically, one or more depth sensors/cameras are used to monitor the OR workflow and provide the captured depth images as inputs to the disclosed bed occupancy detection system. The disclosed bed occupancy detection system is configured to generate 3D point clouds of bed objects detected in the received depth images and subsequently extract a set of geometric features from each 3D point cloud of a bed object. The disclosed bed occupancy detection system further includes a trained binary classifier, e.g., a decision tree classifier trained on a training dataset that includes both a first class of training samples of human-occupied bed objects and a second class of training sample of empty bed objects or bed occupied by non-human objects. When activated, the disclosed bed occupancy detection system apples the trained binary classifier to the 3D point cloud of a hospital bed to infer whether the bed is occupied by a patient or not with high accuracy and without the help of RGB information.

The disclosed bed occupancy detection system and technique can be used to detect two types of OR workflow events in real time during a surgical procedure: (1) at the beginning of a surgical procedure when a patient on a hospital bed is being pushed into the OR and (2) at the end of a surgical procedure when a patient on a hospital bed is being pushed out of the OR, and subsequently trigger real-time event alerts when such events are detected. These real-time OR workflow alerts can then be used for automated people coordination purposes. Note that the disclosed bed occupancy detection system and technique can operate in tandem with the previously-disclosed 3D object detection and tracking system capable of detecting at the beginning of a surgical procedure when a hospital bed is entering the OR, and toward the end the surgical procedure when the hospital bed is exiting the OR. These bed detections can then activate the disclosed bed occupancy detection system to determine whether a patient occupies the detected bed entering or exiting the OR. Moreover, the disclosed bed occupancy detection system and technique can operate in an offline mode to process the recorded OR depth-camera videos to determine at which times these OR workflow events took place during the surgical procedure. Furthermore, the disclosed bed occupancy detection system and technique can be used to perform the occupancy detections either when the hospital bed is in motion or when the hospital bed is stationary. The disclosed bed occupancy detection system and technique can be readily applied to determining whether a surgical table in the OR is empty or occupied by a patient, and therefore not limited to just the scope of detecting the occupancy of a hospital bed.

The disclosed bed occupancy detection system and technique rely exclusively on depth sensor/camera outputs and extracted 3D point cloud data without the need for RGB/color information. As a result, the disclosed bed occupancy detection system and technique provide significantly improved privacy protection. Moreover, compared with existing RGB/color-based techniques, the disclosed bed occupancy detection system and technique use the geometric features of human body when lying flat extracted from the point clouds to differentiate from other non-human objects. Such geometric features remain distinguishable and therefore are not affected when the patient is under a blanket or bed sheet. In contrast, the existing RGB-image or other 2D image detectors will fail under such circumstances.

In one aspect, a process for determining if a bed object inside an operating room (OR) is occupied by a patient is disclosed. During operation, the process segments a three-dimensional (3D) point cloud of a bed object within a depth image captured in an OR into a plurality of segments in both a length direction and a width direction of the bed object. Next, the process extracts a set of geometric features from the plurality of segments. The process subsequently applies a binary classifier to the set of geometric features to classify the bed object as either being occupied by a patient or not being occupied by a patient.

In some embodiments, prior to segmenting the 3D point cloud of the bed object, this process receives the depth image among a sequence of depth images captured in the OR.

In some embodiments, the sequence of depth images is captured by a depth camera installed in the OR, and the process extracts the 3D point cloud from the depth image by projecting each 2D pixel (u, v) and the corresponding distance value d(u, v) in the depth image into a 3D point (x, y, z) in a 3D-coordinate system aligned with the depth camera.

In some embodiments, the process segments the 3D point cloud of the bed object into a plurality of segments by: (1) segmenting the 3D point cloud along the length direction of the bed object into a first plurality of equal-sized segments; and (2) segmenting the 3D point cloud along the width direction of the bed object into a second plurality of equal-sized segments.

In some embodiments, the process extracts the set of geometric features from the plurality of segments by: (1) computing a set of standard deviations of height values using the z-component of a subset of the 3D point cloud associated with each segment of the first plurality of equal-sized segments along the length direction; and (2) computing a set of standard deviations of height values using the z-component of a subset of the 3D point cloud associated with each segment of the second plurality of equal-sized segments along the width direction.

In some embodiments, the number of segments in the first plurality of equal-sized segments is three, and wherein segmenting the 3D point cloud along the length direction into three equal sections allows for capturing unique height distributions in each section of the human body in the length direction when a person is lying flat on the bed object.

In some embodiments, the number of segments in the second plurality of equal-sized segments is two, and wherein segmenting the 3D point cloud along the width direction into two equal sections allows for capturing a geometrical symmetry along the width direction when a person is lying flat on the bed object.

In some embodiments, prior to segmenting the 3D point cloud of the bed object, the process further includes the steps of preprocessing the 3D point cloud by: (1) computing an average height value of the z-component of the 3D point cloud; and (2) removing a subset of 3D points in the 3D point cloud with the z-component values smaller than the computed average height value.

In some embodiments, the process extracts the set of geometric features by additionally computing an overall standard deviation of height value using the z-component of the remaining 3D points in the 3D point cloud after preprocessing the 3D point cloud. The process then combines the overall standard deviation as an additional geometric feature with the set of geometric features extracted from the plurality of segments.

In some embodiments, the process applies a decision tree classifier to the set of extracted geometric features to classify the bed object, which outputs either a positive classification indicating the bed object is occupied by a patient or a negative classification indicating the bed object is not occupied by a patient.

In some embodiments, the process applies the binary classifier to classify the bed object as the negative classification by identifying and classifying a set of false positives associated with the bed object as the negative classification.

In some embodiments, the set of false positives includes scenarios when the bed object is occupied by various non-human objects including: one or more boxes, one or more OR equipments, and one or more blankets.

In some embodiments, prior to applying the binary classifier to classify the bed object, the process constructs a training dataset from a set of depth-camera videos capturing OR workflow, wherein the training dataset includes a first class of labeled samples of occupied bed scenarios and a second class of samples of non-occupied bed scenarios. Next, the process trains the binary classifier using the training dataset.

In some embodiments, the non-occupied bed scenarios include both empty bed scenarios and non-human-object occupied bed scenarios.

In some embodiments, the training dataset includes training samples extracted from depth images of a bed object captured from multiple viewing angles that include at least a top-view of the bed object.

In some embodiments, the bed object includes: (1) a hospital bed used for transporting a patient into and out of the OR; and (2) a surgical table used to operate a patient during a surgical procedure in the OR.

In some embodiments, using geometric information extracted from the depth images of the bed object to classify the bed object in the OR as either being occupied or not being occupied by a patient does not require color images of the OR, thereby providing significantly improved privacy protection of the patient.

In another aspect, an apparatus for determining if a bed inside an operating room (OR) is occupied by a patient is disclosed. This apparatus includes one or more processors and a memory coupled to the one or more processors. Moreover, the memory stores instructions that, when executed by the one or more processors, cause the apparatus to: (1) receive a three-dimensional (3D) point cloud of a bed object within a depth image captured inside an OR; (2) segment the 3D point cloud of the bed object into a plurality of segments in both a length direction and a width direction of the bed object; (3) extract a set of geometric features from the plurality of segments; and (4) apply a binary classifier to the set of geometric features to classify the bed object as either being occupied by a patient or not being occupied by a patient.

In some embodiments, the memory further stores instructions that, when executed by the one or more processors, cause the apparatus to extract the set of geometric features by: (1) segmenting the 3D point cloud along the length direction of the bed object into a first plurality of equal-sized segments; (2) segmenting the 3D point cloud along the width direction of the bed object into a second plurality of equal-sized segments; and (3) computing a standard deviation in height values using a subset of the 3D point cloud associated with each segment in the first plurality of equal-sized segments and each segment in the second plurality of equal-sized segments.

In some embodiments, the memory further stores instructions that, when executed by the one or more processors, cause the apparatus to preprocess the 3D point cloud prior to segmenting the 3D point cloud by: computing an average height value of the z-component of the 3D point cloud; and removing a subset of 3D points in the 3D point cloud with the z-component values smaller than the computed average height value.

In yet another aspect, a system for determining if a bed inside an operating room (OR) is occupied by a patient is disclosed. This system includes: one or more depth cameras installed in the OR; one or more processors coupled to the one or more depth cameras; and a memory coupled to the one or more processors. Moreover, the memory stores instructions that, when executed by the one or more processors, cause the system to: (1) receive a depth image among one or more sequences of depth images captured by the one or more depth cameras; (2) segment the 3D point cloud of the bed object into a plurality of segments in both a length direction and a width direction of the bed object; (3) extract a set of geometric features from the plurality of segments; and (4) apply a binary classifier to the set of geometric features to classify the bed object as either being occupied by a patient or not being occupied by a patient.

In some embodiments, the one or more depth cameras include at least two depth cameras which are installed in the OR to capture depth images of the bed object from multiple viewing angles that include at least a top-view angle.

BRIEF DESCRIPTION OF THE DRAWINGS

The structure and operation of the present disclosure will be understood from a review of the following detailed description and the accompanying drawings in which like reference numerals refer to like parts and in which:

FIG. 3 presents a flowchart illustrating an exemplary process for building a training dataset and training a hospital bed occupancy classifier using the training dataset in accordance with some embodiments described herein.

DETAILED DESCRIPTION

Figure 1:
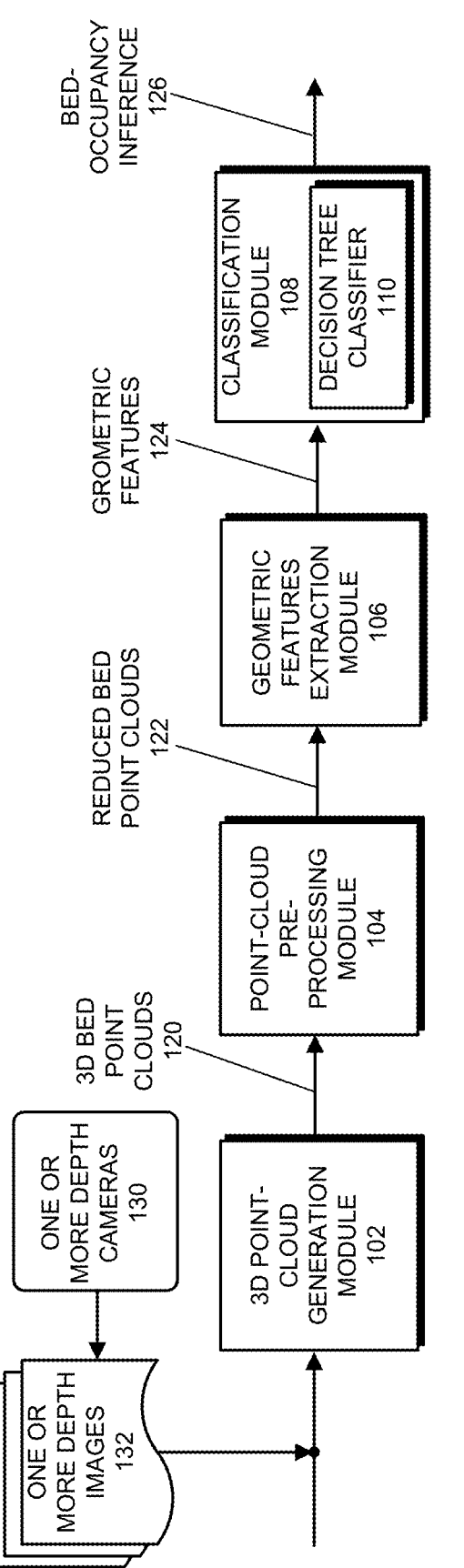
FIG. 1 illustrates a block diagram of a hospital-bed occupancy detection system for determining whether a hospital bed (both stationary and mobile) within an operating room (OR) is occupied by a patient or not in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Terminology

Throughout this patent disclosure, the term "hospital bed" is used to refer to a mobile bed or a stretcher on which a patient is transported into/out of an operating room (OR); whereas the term "surgical table" is used to refer to a stationary table in the OR on which a patient lies during a surgical procedure.

Overview

Disclosed are various operating room (OR) bed occupancy detection systems and techniques based on three-dimensional (3D) point clouds of the hospital beds/surgical tables extracted from depth images of the OR captured by one or more depth cameras installed in the OR. Specifically, one or more depth sensors/cameras are used to monitor the OR workflow and provide the captured depth images as inputs to the disclosed bed occupancy detection system. The disclosed bed occupancy detection system is configured to generate 3D point clouds of bed objects detected in the received depth images and subsequently extract a set of geometric features from each 3D point cloud of a bed object. The disclosed bed occupancy detection system further includes a trained binary classifier, e.g., a decision tree classifier trained on a training dataset that includes both a first class of training samples of human-occupied bed objects and a second class of training sample of empty bed objects or bed occupied by non-human objects. When activated, the disclosed bed occupancy detection system apples the trained binary classifier to the 3D point cloud of a hospital bed to infer whether the bed is occupied by a patient or not with high accuracy and without the help of RGB information.

The disclosed bed occupancy detection system and technique can be used to detect two types of OR workflow events in real time during a surgical procedure: (1) at the beginning of a surgical procedure when a patient on a hospital bed is being pushed into the OR and (2) at the end of a surgical procedure when a patient on a hospital bed is being pushed out of the OR, and subsequently trigger real-time event alerts when such events are detected. These real-time OR workflow alerts can then be used for automated people coordination purposes. Note that the disclosed bed occupancy detection system and technique can operate in tandem with the previously-disclosed 3D object detection and tracking system capable of detecting at the beginning of a surgical procedure when a hospital bed is entering the OR, and toward the end the surgical procedure when the hospital bed is exiting the OR. These bed detections can then activate the disclosed bed occupancy detection system to determine whether a patient occupies the detected bed entering or exiting the OR. Moreover, the disclosed bed occupancy detection system and technique can operate in an offline mode to process the recorded OR depth-camera videos to determine at which times these OR workflow events took place during the surgical procedure. Furthermore, the disclosed bed occupancy detection system and technique can be used to perform the occupancy detections either when the hospital bed is in motion or when the hospital bed is stationary. The disclosed bed occupancy detection system and technique can be readily applied to determining whether a surgical table in the OR is empty or occupied by a patient, and therefore not limited to just the scope of detecting the occupancy of a hospital bed.

The disclosed bed occupancy detection system and technique rely exclusively on depth sensor/camera outputs and extracted 3D point cloud data without the need for RGB/color information. As a result, the disclosed bed occupancy detection system and technique provide significantly improved privacy protection. Moreover, compared with existing RGB/color-based techniques, the disclosed bed occupancy detection system and technique use the geometric features of human body when lying flat extracted from the point clouds to differentiate from other non-human objects. Such geometric features remain distinguishable and therefore are not affected when the patient is under a blanket or bed sheet. In contrast, the existing RGB-image or other 2D image detectors will fail under such circumstances.

Point-Cloud-Based Hospital-Bed Occupancy Detection System

FIG. 1 illustrates a block diagram of a disclosed hospital-bed occupancy detection system 100 (also referred to as "bed occupancy detection system 100" or "occupancy detection system 100" hereinafter) for determining whether a hospital bed (both stationary and mobile) within an operating room (OR) is occupied by a patient or not in accordance with some embodiments described herein. As can be seen in FIG. 1, occupancy detection system 100 can include at least the following functional modules: (1) a three-dimensional (3D) point-cloud generation module 102; (2) a point-cloud pre-processing module 104; (3) a geometric features extraction module 106; and (4) a point-cloud classification module 108, which are coupled to each other in the order shown. During operation, the disclosed occupancy detection system 100 can begin when point-cloud generation module 102 receives raw depth images 132 from one or more depth cameras 130 installed in the OR. At a given decision/inference time point, 3D point-cloud generation module 102 is configured to receive one or more raw depth images 132 of the OR in a continuous sequence of raw depth images 132 of the OR captured by the one or more depth cameras 130 as inputs and generate one or more 3D point clouds 120 of the hospital bed (or simply "bed point clouds 120" or "3D point clouds 120") for the given decision/inference time point as output.

Note that the one or more depth cameras 130 include at least one depth camera, but can also include two or more depth cameras. In some embodiments, when more than one depth camera 130 is installed and employed, the multiple depth cameras can provide at least a top-view and a side-view of the OR scenes. Each of the one or more depth cameras 130 can include a time-of-flight (ToF) sensor using an infrared light source. In other embodiments, each of the one or more depth cameras 130 can include a Light-Detection-And-Ranging (LiDAR) sensor. Note that the one or more depth cameras 130 can be but not necessarily a part of occupancy detection system 100. Moreover, each of the one or more depth cameras 130 can be a component of an integrated RGB-D camera.

In some embodiments, to detect a hospital bed or any bed object within a given depth image 132 of the OR, 3D point-cloud generation module 102 can be coupled to or directly incorporating (not explicitly shown) a point-cloud-based 3D object detection and tracking module/system described in a co-pending U.S. patent application Ser. No. 17/741,812, entitled "Operating Room Objects And Workflow Tracking Using Cameras" and filed on May 11, 2022, the contents of which are hereby incorporated by reference as a part of this patent document. Note that this incorporated 3D object detection and tracking module/system is configured to detect both events when a hospital bed is entering and when the hospital bed is leaving the OR based on the captured raw depth images 132, and can continue to track the movement of a detected hospital bed through a sequence of depth images 132. However, the incorporated 3D object detection and tracking module/system is not capable of detecting and/or determining whether the hospital bed is entering or leaving the OR carrying a patient or not. By combining the previously-disclosed 3D object detection and tracking module/system with the disclosed bed occupancy detection system (either directly incorporating the 3D object detection and tracking module/system or indirectly using the outputs from the 3D object detection and tracking module/system that receives the same raw depth images 132 as input), the combined system and technique can determine in real-time and with certainty whether a patient is also entering or leaving the OR together with the detected hospital bed, which are both high priority OR workflow events for detection.

Referring back to FIG. 1, note that when the one or more raw depth images 132 include a single raw depth image 132, a single bed point cloud 120 can be obtained by projecting each 2D pixel (u, v) and the corresponding measured depth/distance value d(u, v) in the single raw depth image 132 of the detected hospital bed into a 3D point in a 3D-coordinate system (x, y, z) aligned with depth camera 130 using a known lens model of depth camera 130. However, when there are two or more depth cameras 130 and thus two or more raw depth images 132 received by 3D point-cloud generation module 102 at a given decision time point, two or more bed point clouds 120 are generated by 3D point-cloud generation module 102 from the two or more received raw depth images 132, which can include at least one top-view image and at least one side-view image of the OR and the detected hospital bed.

When setting up the one or more depth cameras 130 or the integrated RGB-D cameras in the OR, it has been found that the camera setup locations, camera angles, and the number of cameras used can have significant effects on the quality of the generated bed point clouds 120 and consequently, on the interference accuracies of occupancy detection system 100. For example, it is noticed that when a single depth camera 130 is set up with a lower position/viewing angle to provide only a side-view of the hospital bed, it can be more challenging to generate a complete point cloud 120 of the hospital bed with a patient on top of the bed because the hospital bed may be occluded by people walking in front of the bed and/or by an equipment that is moved along with the bed. In contrast, when a single depth camera 130 is set up at a higher position and directly pointing to the OR doorway/ entrance, the captured depth images 132 can provide a top-view of the OR doorway/entrance, and therefore capable of capturing full point clouds of the hospital bed entering and exiting the OR. Hence, if only one depth camera 130 is available in conjunction with occupancy detection system 100, it is desirable to position the depth camera 130 at a higher viewing angle and directly pointing to the OR entrance/doorway to capture the top-view images of the OR scenes. Generally speaking, it can be more beneficial to install more than one depth camera 130 in the OR to independently capture multiple views of the OR scenes, including at least a top-view of the OR scenes and one or more side-views of the OR scenes. These multiple views of the captured depth images of the same OR scenes can be combined to enhance both the 3D-coordinates precisions and completeness of the generated point clouds 120 of the captured hospital bed within the OR.

As can be seen in FIG. 1, the one or more 3D point clouds 120 of the hospital bed is received by point-cloud pre-processing module 104, which is configured to remove a subset of 3D points in 3D point clouds 120 that are below the hospital bed surface. In some embodiments, pre-processing each of the 3D point clouds 120 to remove 3D points below the bed surface includes removing those 3D points $(x, y, z)$ that have z-values below the computed mean z-value of given point cloud 120. Because in a calibrated 3D-coordinate system of a given 3D bed point cloud 120, z values are measured to represent the height of each 3D point in the Z-axis perpendicular the ground surface of the OR, pre-processing module 104 is essentially used to remove the entire (lower z) section of the given bed point cloud 120 below the mean height of the given bed point cloud 120. Note that these removed 3D points from below the mean height are generally unrelated to a patient/person but generally associated with the shape of the bottom of the hospital bed and possibly objects attached to the bottom of the hospital bed. Point-cloud pre-processing module 104 subsequently outputs one or more reduced bed point clouds 122.

Next, the one or more reduced bed point clouds 122 are received by geometric features extraction module (or simply "feature extraction module") 106 which is configured to extract a set of geometric features 124 from each of the one or more reduced bed point clouds 122 that can be used to determine whether the hospital bed captured in a given depth image 132 is occupied by a patient or not. In some embodiments, feature extraction module 106 is configured to extract a set of 6 features 124 from each of the one or more reduced bed point clouds 122 corresponding to the one or more depth cameras 130 capturing of the hospital bed from one or more viewing angles. Note that each of the 6 geometric features 124 is extracted from a different portion of a given reduced bed point cloud 122. As a result, having more than one reduced bed point cloud 122 for the feature extraction operation may be beneficial because, in case when a portion of one reduced bed point cloud 122 is occluded by a person or an object, another reduced bed point cloud 122 can be used to generate a corresponding feature. We now describe in detail how to extract a set of geometric features 124 from each of the one or more reduced bed point clouds 122.

Figures 2A, 2B:
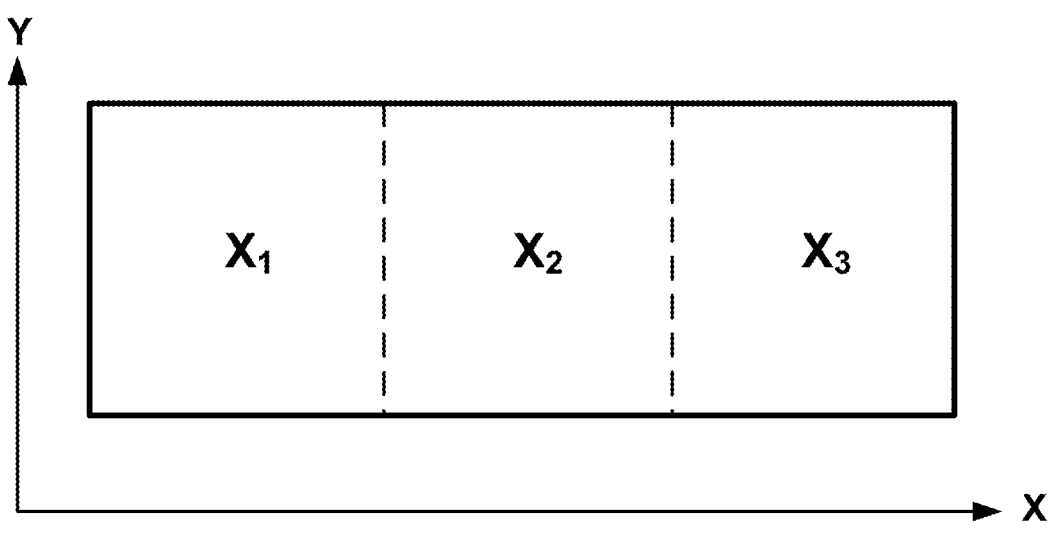
FIG. 2A illustrates segmenting an exemplary bed point cloud along the X-axis into three equal-sized segments in preparation for X-segment feature extraction in accordance with some embodiments described herein.
FIG. 2B illustrates segmenting an exemplary bed point cloud along the Y-axis into two equal-sized segments in preparation for Y-segment feature extraction in accordance with some embodiments described herein.

In some embodiments, feature extraction module 106 is configured to segment the reduced bed point cloud 122 along the length direction (i.e., the long-axis or the X-axis) into 3 segments, e.g., 3 equal-sized segments (namely, $X_1$, $X_2$, and $X_3$). In some embodiments, to generate the 3 X segments, the minimum x-value and the maximum x-value are extracted from the reduced bed point cloud 122, and then the reduced bed point cloud 122 is divided into 3 equal segments by equally partitioning between the minimum x-value and the maximum x-value by three. Next, for each of the three X segments, the standard deviation in height z is computed based on the portion of the point cloud 122 within the given X segment. In this manner, 3 geometric features 124 along the length direction/X-axis are generated. FIG. 2A illustrates segmenting an exemplary bed point cloud 202 along the X-axis into three equal-sized segments in preparation for X-segment feature extraction in accordance with some embodiments described herein. Specifically, the exemplary bed point cloud 202 represents a top-view of a given reduced point cloud 122 in an X-Y plane of the 3D coordinate system $(x, y, z)$.

In addition to extracting the three X-segment features, feature extraction module 106 is further configured to separately segment the reduced bed point cloud 122 along the width direction (i.e., the short-axis or the Y-axis) into 2 equal-sized segments (namely $Y_1$ and $Y_2$). In some embodiments, to generate the two Y segments, the minimum y-value and the maximum y-value are extracted from the reduced bed point cloud 122, and then the reduced bed point cloud 122 is divided into two equal Y segments by equally dividing between the minimum y-value and the maximum y-value. Next, for each of the two Y segments, the standard deviation in height z is computed based on the portion of the point cloud 122 within the given Y segment. As a result, 2 Y-segment features 124 along the width direction/Y-axis are generated. FIG. 2B illustrates segmenting an exemplary bed point cloud 202 along the Y-axis into two equal-sized segments in preparation for Y-segment feature extraction in accordance with some embodiments described herein. Finally, the standard deviation in height z for the entire reduced bed point cloud 122 is computed, thereby generating another (the sixth) geometric feature in the set of geometric features 124.

Returning to FIG. 1, the set of geometric features 124 is received by hospital bed classification module 108 (or simply "classification module 108"), which is configured to process the set of geometric features 124 and generate a binary classification/inference on the received one or more depth images 132 of the hospital bed at the given decision time point as either being occupied by the patient (also referred to as an "OP classification/inference" or simply "OP class" hereinafter) or not being occupied by the patient (also referred to as a "NOP classification/inference" or simply "NOP class"). In some embodiments, classification module 108 processes the set of geometric features 124 by applying a decision tree classifier 110 (also referred to as "decision tree model 110") to the set of geometric features 124 and generates a bed-occupancy inference 126, which classifies the generated 3D bed point clouds 120 at the given time point as either an OP class (or an "1" output value) or a NOP class (or a "0" output).

Note that some benefits of using a decision tree classifier within classification module 108 over using a complex deep neural network (DNN) classifier includes: (1) a decision tree is proven to be a good binary classifier on small input dimensions, and thus fully capable of processing the set of geometric features to distinguish between a patient-occupied bed and a bed not occupied by a patient; and (2) a decision tree classifier is lightweight with very low computational requirement, and therefore can be installed in-situ (i.e., embedded inside an OR depth camera/RGB-D camera) and run on the depth sensor so that the depth-image processing and occupancy detections can be performed in the OR. Using the decision tree classifier therefore eliminates the need for a separate complex and expensive system that uses a DNN to process the geometric features 124, which is generally not affordable for many hospitals. However, these hospitals can easily afford an intelligent depth sensor with lower computational power but can still sufficiently and efficiently implement a decision tree classifier. We describe in more detail the construction, the training and the inference operation of decision tree classifier 110 below. However, other embodiments of bed occupancy detection system 100 can use other types of classifiers other than a decision tree classifier (e.g., a DNN model) within classification module 108 to process the set of geometric features 124 and make proper OP or NOP inferences, without departing from the scope of the present disclosure.

Note that the proposed technique of X-axis segmentation of the bed point cloud is based on the observations and therefore reflects the characteristics of human body geometry. When a patient lies down on a hospital bed, e.g., on his/her back flat, different sections of the patient's body will exhibit unique human geometric/contour features. In particular, the $X_1$ segment approximately corresponds to the head section of the human body, the $X_2$ segment approximately corresponds to the torso/middle section of the human body, and the $X_3$ segment approximately corresponds to the leg/lower section of the human body, wherein each of the three segments has at least one distinct human geometric/contour feature. For example, the $X_1$ segment includes a unique dip due to height change from the head to the neck, whereas the $X_3$ segment contains the patient feet that cause variations in heights as a result of toes of the feet pointing upward. Furthermore, the $X_2$ segment which contains the middle section is expected to be generally higher than other parts of the human body (i.e., $X_1$ and $X_2$ segments). After the standard deviation has been calculated for each of the X-segment against the mean height of the entire reduced bed point cloud 122, the above-described unique geometric feature within each X-segment is embedded into the corresponding standard deviation values.

An important insight behind partitioning a bed point cloud into two equal Y segment is that, when a patient is lying on the hospital bed flat, there is usually symmetry along the Y-axis, referred to as the "Y symmetry." Note that a pillow placed on the hospital bed, regardless of its shape, is usually also symmetric along the Y-axis. Hence, using two equal sections along the Y-axis to generate the two corresponding standard deviations can capture this Y symmetry of the human body, which is then embedded into the two Y-segment features (i.e., the corresponding two standard deviations). In contrast, a random OR objection such as a piece of equipment laid on the hospital bed typically does not possess the same Y symmetry, and therefore can be distinguished from a patient/person on the hospital bed based on the two proposed Y-segment features.

Another insight behind partitioning a bed point cloud into the multiple X segments and Y segments and extracting standard deviations in height z from these segments is to obtain the unique height distribution and the associated unevenness in each section of the human body (i.e., the unique human contour) within a given X or Y segment of the point cloud, assuming the patient is lying flat on the hospital bed. Because these extracted human geometric features do not exist in other OR objects such as OR equipments or boxes placed on the hospital bed, the 6 extracted geometric features, separately and collectively can be used to differentiate from and discriminate against other OR scenarios of a hospital bed, such as when the hospital bed is not occupied by a patient (i.e., an empty bed) or when the hospital bed is occupied by a non-human object.

For example, if a large object such as a very large box is placed on the hospital bed across the entire length, the extracted standard deviation values when applying the above X segmentations will be distinctively different from the corresponding standard deviation values of a human, because the large box object does not possess the human geometric features. As another example, a large box or a piece of equipment positioned on the hospital bed generally does not have the size to occupy all 3 X-segments, and therefore will have zero standard deviations in those unoccupied segments. Consequently, the three extracted X-segment features can be used to distinguish a human on the hospital bed from such non-human objects left on the hospital bed. As such, we may refer to the process of distinguishing a human on the hospital bed from a non-human object on the hospital bed using the extracted X-segment features as "X feature tests." However, if there is such a large object that occupies all 3 X segments and can pass the "X feature tests," the two extracted Y-segment features can then be used to distinguish such an extra large non-human object on the hospital bed from a real patient on the hospital bed. Similarly, we may refer to the process of distinguishing a human on the hospital bed from a non-human object on the hospital bed using the extracted Y-segment features as "Y feature tests." Note that if a certain object can pass both X feature tests and Y feature tests (e.g., a large human-shaped dummy), the sixth geometric feature, i.e., the standard deviation in z computed for the entire reduced bed point cloud 122 can be used to differentiate such an object from a real patient/person. Note that the standard deviation in z for the entire bed point cloud can be used to eliminate false positives (FPs) caused by those objects that satisfy both X feature tests and Y feature tests, but have an overall height distribution/contour significantly different from a human being (e.g., a human-shaped dummy with 1-meter chest height when laying flat).

As a variation to extracting 3 geometric features from 3 equal X segments shown in FIG. 2A, 2 X-segment features based on the standard deviation in z can be extracted after segmenting each reduced bed point cloud 122 along the X-axis into 2 equal-sized segments. It should be noted that this embodiment is likely to separate the middle section of the human body into the two X segments, instead of treating the middle section in its entirety. However, due to the above-described unique height distributions in the middle section of a person, it is preferable to separate the middle section of the patient from the head-neck section and leg-feet section of the patient, and treat the middle section independently from the other body sections.

As another variation to the 3 equal X segments shown in FIG. 2A, it is possible to segment each reduced bed point cloud along the X-axis into more than 3 X segments. For example, some embodiments can segment each point cloud along the X-axis into N equal-sized segments, wherein N>3. It should be noted that these embodiments of using more than 3 X segments and geometric features can create an inaccurate representation for shorter patients. This is because the first and/or the last X segment in such an embodiment where N>3 may not be filled up by or even contain a portion of a short patient, and as a result, the extracted geometric features in these end segments cannot accurately represent such a patient.

As a variation to extracting 2 geometric features from 2 equal Y segments shown in FIG. 2B, more than 2 (e.g., 3) Y-segment features based on the standard deviation in z can be extracted after segmenting each reduced bed point cloud along the Y-axis into more than 2 (e.g., 3) equal-sized segments. It should be noted that the embodiment of using 3 equal-sized Y segments does not retain the body Y symmetry reflected in the embodiment of 2 equal-sized Y segments of FIG. 2B, and therefore can result in higher false positives than the embodiment of FIG. 2B.

Building a Training Dataset and Training the Bed Occupancy Classifier

To build an accurate point cloud classifier (e.g., a decision tree classifier) to be implemented within classification module 108 to process the set of extracted geometric features 124 with high confidence, it is necessary to train the point cloud classifier with a diverse training dataset that includes a wide variety of scenarios involving a hospital bed in an OR during a surgical procedure. In some embodiments, to build such a diverse training dataset, a set of OR surgical videos captured by depth cameras is collected as training videos. Next, for each training video, one or more sequences of depth images of the hospital bed are identified and used to generate the corresponding point clouds. Moreover, each identified depth image of the hospital bed is carefully labeled with one of the two classifications (i.e., OP and NOP classifications) by one or more human annotators, which also provides the same classification to the corresponding extracted point cloud. Next, a set of geometric features (i.e., the proposed 6 geometric features) is extracted from each generated bed point cloud using the geometric feature extraction techniques described in conjunction with bed occupancy detection system 100 of FIG. 1. For example, each generated bed point cloud is segmented and a standard deviation based on the z-values is computed for each segment.

Next, the extracted geometric features are labeled with the corresponding classification of the corresponding point cloud/depth image. This means that for each depth image selected for constructing the training dataset, each extracted feature is labeled as one of the two classes: OP and NOP. Hence, when the proposed 6 geometric features are implemented, 6 labeled samples are generated for each selected depth image. As an example, to generate a training dataset with 600 training samples, 100 representative frames/depth images can be selected from one or more surgical videos used as the training data source.

In some embodiments, to reduce training data bias, relatively equal numbers of training samples/images are collected for the two output classes: OP and NOP. Specifically for the training samples/images generated for the NOP class, it is necessary to include samples from not only pure empty bed scenarios but also various FP scenarios of the hospital bed when the bed is occupied by various non-human objects, such as boxes, OR equipments, piles of blankets, an extra mattress, among others. Note that even for empty bed scenarios, certain hospital beds are constructed with railings which can cause FPs even when the beds are empty. Therefore, the training samples/images should include such hospital beds so that they can be differentiated from regular occupied beds by the trained detection model/classifier. As mentioned above, all or near all of the potential FP scenarios should be identified and included in the training samples for the NOP class. When these FP scenarios are included and properly labeled with the NOP classification in the training dataset, the trained bed-occupancy detection models/classifiers will be capable of differentiating and discriminating them from the true positive (TP) (i.e., beds occupied by patients) scenarios.

In some embodiments, when constructing a training dataset using representative images from a training surgical video, it is not desirable to select a set of consecutive video frames from the training video. For example, when a patient is being slowly pushed into the OR, it is clearly lack of efficiency to use the entire action sequence of the patient entering the OR as training images, because each frame within the action sequence has substantially the same information as the other frames in the action sequence. Consequently, including consecutive frames from such an action sequence does not facilitate to diversify the training dataset. Instead, it is desirable to choose representative image samples throughout the training surgical video more evenly and judiciously. For example, if the hospital bed enters/exits the OR at a fast speed, a set of frames spaced out by a short interval can be taken from the captured action sequence as training samples. In contrast, if the hospital bed enters/exits the OR slowly, a set of frames separated by a long interval will be selected from the captured action sequence.

In some embodiments, choosing sample frames from a given training video to build the training dataset involves choosing only those video frames when the hospital bed has become maximized in size. For example, when a patient is being pushed into the OR on a hospital bed and being captured by the video frames, the bed may start to appear partially visible but at a point become fully visible. The training data should be collected when the bed becomes fully visible in the frames. In other words, those frames in the training video that include a partial bed should be excluded from the training dataset because they do not fit the classifier models within the disclosed bed occupancy detection system 100. This means that only a middle portion of a training video is used to construct the training dataset. Specifically, the middle portion of the training video for extract data sample may start when the hospital bed has just fully entered the depth camera view, continue to present under the depth camera view, and end when the bed is being pushed away and start to exit the captured video frames. This also means that the portions of the training video before and after the middle portion will not be used.

Moreover, when collecting training data, it is necessary to collect training data generated by depth sensors/cameras set up with different camera views/angles (e.g., one or more top-views and one or more side-views). Note that data from multiple camera views/angles are highly desirable because a single depth sensor/camera installed on a lower camera angle may only capture a side-view of the hospital bed/patient, which is insufficient to be used to extract a complete set of (e.g., the six) geometric features 124. Furthermore, a bed occupancy classifier/model trained with a training dataset that is collected from multiple camera views/angles of multiple depth sensor/camera setups in the OR can also be operable with different camera views and process data from depth cameras installed at different locations in the OR. In other words, when deployment in an OR, such an occupancy classifier/model trained on training data collected from multiple camera views/angles is insensitive and independent of how the depth camera is installed in the OR. This means that once a single bed occupancy classifier is constructed and trained, it can be deployed in different ORs of different hospitals with comparable performances.

In some embodiments, after constructing the training dataset, the training dataset is split into a training set (e.g., 80% of the total training dataset) and a validation set (e.g., 20% of the total training dataset). Note that the validation dataset can be used to remove ineffective features, even when they show high variances. For example, more than 3 X segments have been shown to be ineffective. The validation set has helped to eliminate ineffective features and reach at the disclosed 6-feature-based occupancy detection model.

FIG. 3 presents a flowchart illustrating an exemplary process 300 for building a training dataset and training a hospital bed occupancy classifier using the training dataset in accordance with some embodiments described herein. In one or more embodiments, one or more of the steps in FIG. 3 may be omitted, repeated, and/or performed in a different order. Accordingly, the specific arrangement of steps shown in FIG. 3 should not be construed as limiting the scope of the technique.

Process 300 may begin by collecting a set of OR work-flow videos as training videos, wherein each of the OR video is captured by a depth camera (step 302). Next, for each training video in the set of OR videos, process 300 identifies a set of representative frames of depth images that include a full view of the hospital bed (step 304). In some embodi-ments, the set of representative frames includes a selected sequence of frames representing a motion sequence of the hospital bed after the bed has just fully entered the OR, continue to present under the depth camera view, and end when the bed is being pushed away and start to exit the captured video frames. As mentioned above, the selected sequence of frames may not necessarily be consecutive, but can be spaced out by a given time interval. Note that each training video can include more than one such motion sequence, and therefore the set of representative frames can include a selected sequence of frames at the beginning of the surgical procedure when the patient is being pushed into the OR on top of the hospital bed, and another selected sequence of frames at the end of the surgical procedure when the patient is being pushed out of the OR on top of the hospital bed.

For each depth image in the set of representative frames including the hospital bed, the depth image is labeled with either an OP classification or a NOP classification based on whether the hospital bed is occupied by a human (step 306). This step essentially separates the set of representative frames into the two data classifications. As mentioned above, in order to reduce data bias, it is necessary to maintain a relatively equal number of training samples/depth images for each data class. Moreover, when constructing the training samples/images for the NOP class, it is necessary to include samples from both pure empty bed scenarios and various FP scenarios when the bed is occupied by various non-human objects, such as boxes of various sizes, OR equipments, piles of blankets, an extra mattress, etc., so that these FP scenarios can be differentiated and discriminated from the TP scenarios.

Next, for each labeled depth image, process 300 generates a corresponding point cloud for the detected hospital bed in the labeled depth image (step 308). For each labeled depth image and the extracted point cloud of the hospital bed in the depth image, process 300 extracts a set of geometric features from the bed point cloud using the feature-extraction tech-niques described above (step 310). For example, extracting the set of geometric features from the bed point cloud may include: (1) removing the portion of the bed point cloud below the bed surface; (2) independently segmenting the bed point cloud along the X-axis and the Y-axis; (3) extracting a geometric feature based on the standard deviation of the z-values for each of the X-segment and Y-segment of the reduced bed point cloud; and (4) extracting an additional geometric feature based on the standard deviation in z for the entire reduced bed point cloud. Subsequently, process 300 labels the set of extracted geometric features with the same OP or NOP classification as the associated labeled depth image, thereby generating a set of labeled samples for the training dataset (step 312). Note that the sequence of steps 308-312 is repeated for the set of representative frames to generate the full training dataset, which is subsequently split into a training set and validation set. Next, process 300 trains a bed occupancy classifier using the generated training dataset (step 314). For example, the bed occupancy classifier can include a decision tree classifier further described below. Training a Decision Tree (DT) Model Using the Training Dataset In some embodiments, constructing a decision tree clas-sifier 110 with the above-described training dataset tech-niques can start by choosing one of the geometric features and a random seed for the chosen feature at the root node. Note that choosing a different starting geometric feature or a different random seed will give rise to a different DT classifier. In some embodiments, the decision to split at the root node is based on a bed Y-symmetry check, i.e., using one of the two above-described Y features in the set of 6 extracted geometric features. The rationale is that, when the bed is already symmetric in Y-axis, it meets a basic condition for the OP classification. However, a split decision based on other extracted geometric features (e.g., using one of the three above-described X features) at the root node can be used, which will generate a different DT classifier. In some embodiments, a seed value for the chosen feature is selected to cause the maximum possible differentiation/split between the two classes that made up the full set of training data. In this manner, the root node provides the highest differentia-tion strength for the two classes of training data. Next, the sub-nodes are used to fine-tune the DT classifier with split data samples and the set of extracted geometric feature.

Generally speaking, the split decisions at the root node and the subsequent nodes (i.e., the sub-nodes) are selected based on the Gini index and the Gini impurity. This means that the training process will select a feature among the set of geometric features, and a corresponding splitting value/condition at each level (both the root node and each of the sub-node) to minimize the Gini impurity computed based on the available training samples. More specifically, this Gini-impurity-based approach uses the Gini index split to check the Gini impurity associated with each geometric feature among the set of geometric features, and subsequently selects the geometric feature which has the lowest associated Gini impurity and features which have their Gini index closest to 0.5 to split the training dataset into two halves, so that they can be further processed in the next tree stage/level. Hence, at each stage/level of the decision tree, the set of geometric features is sorted based on corresponding Gini indices. For a selected geometric feature at a given node, a corresponding Gini impurity is calculated for the corre-sponding training data split. When the calculated Gini impurity at the given node based on the selected geometric feature is close to 0, it is an indicator that the selected feature effectuates a good data classification. As can be seen the exemplary DT classifier training process illustrated below in conjunction with FIGS. 4A-4E, the Gini value for each node is controlled to be no greater than 0.5 and no further split is made when the Gini value becomes 0.0. Note that instead of using Gini index and Gini impurity to create the DT nodes, other embodiments of training the DT classifier can use other metrics to create the root node and subsequent nodes, e.g., information gain, reduction of variance, among others.

Figure 4A:
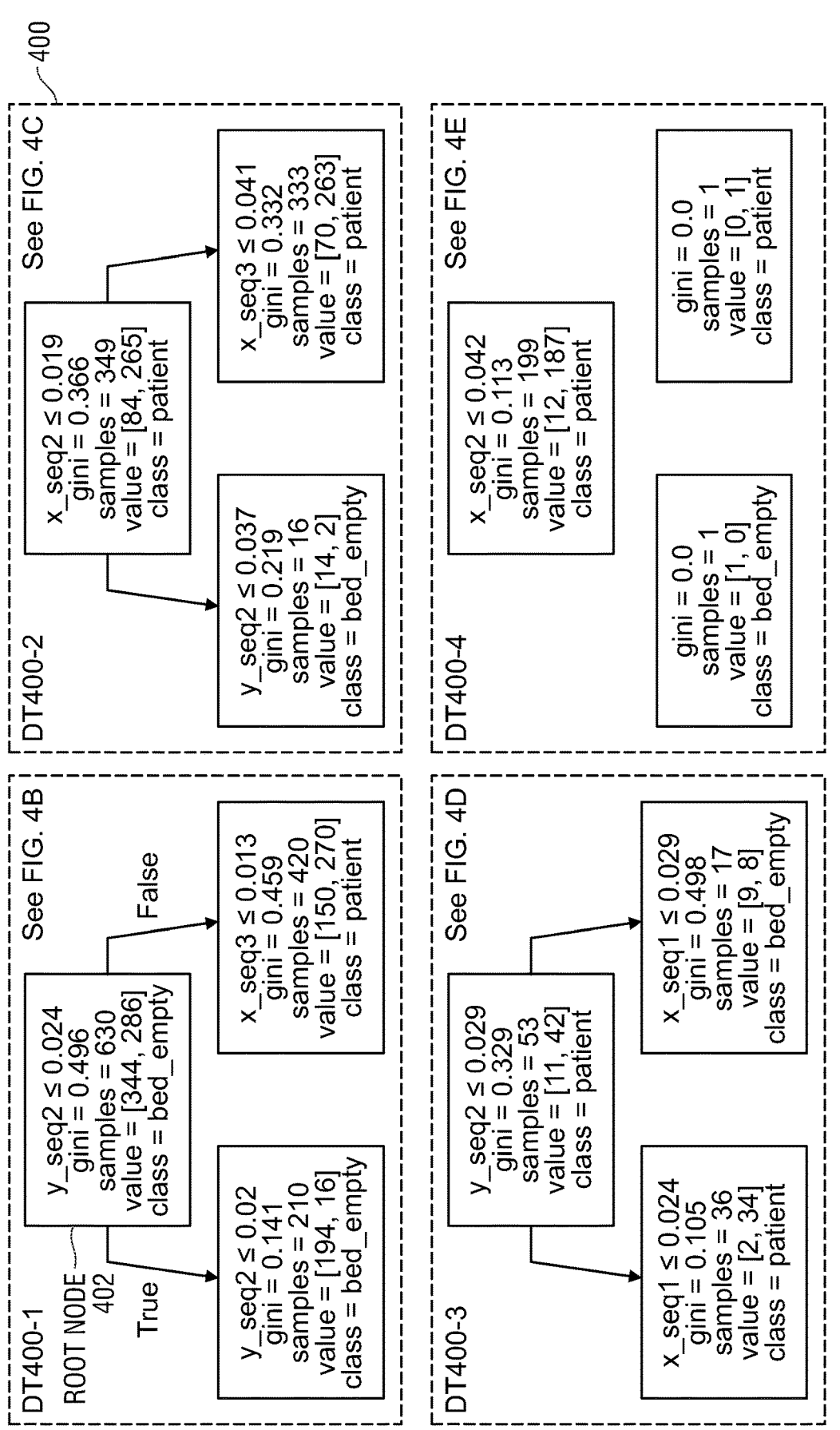
FIG. 4A graphically illustrates an exemplary process of constructing a trained decision tree (DT) model for the bed occupancy detection system of FIG. 1 based a set of training samples in accordance with some embodiments described herein.
Figure 4B:
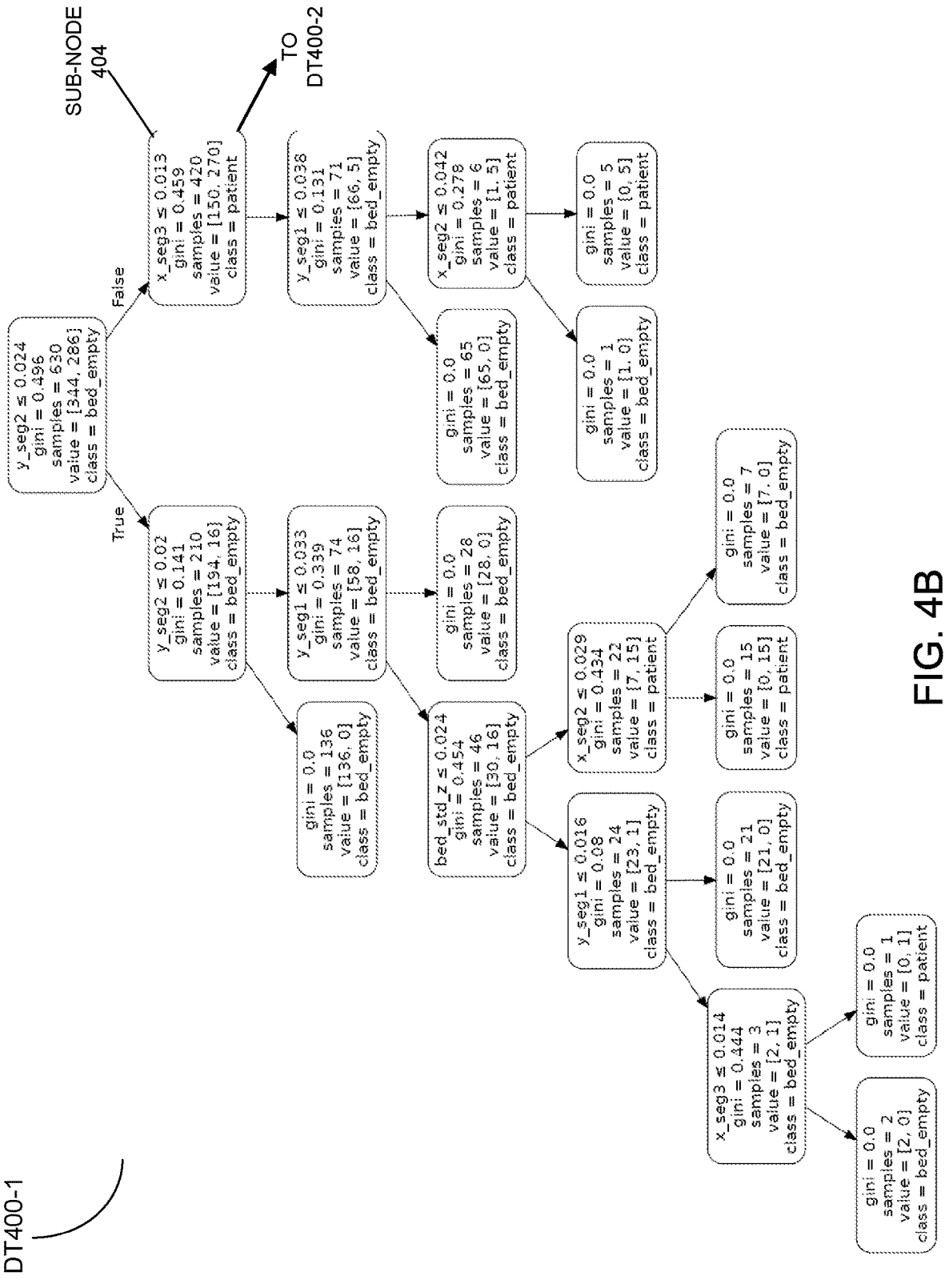
FIGS. 4B-4E illustrate each of the four portions: DT400-1, DT400-2, DT400-3, and DT400-4 of the trained DT classifier in FIG. 4A, respectively with higher resolutions.
Figure 4C:
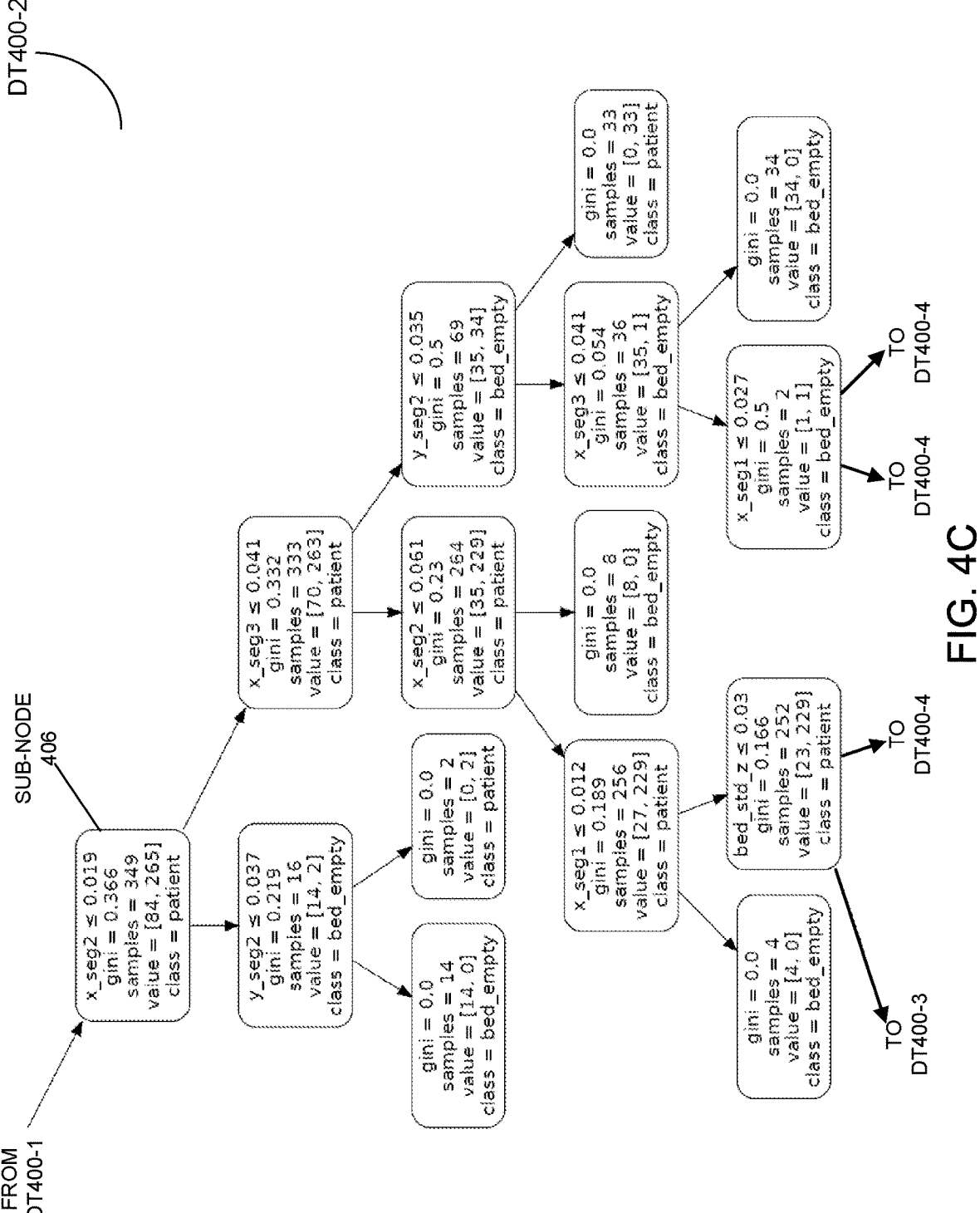
Figure 4D:
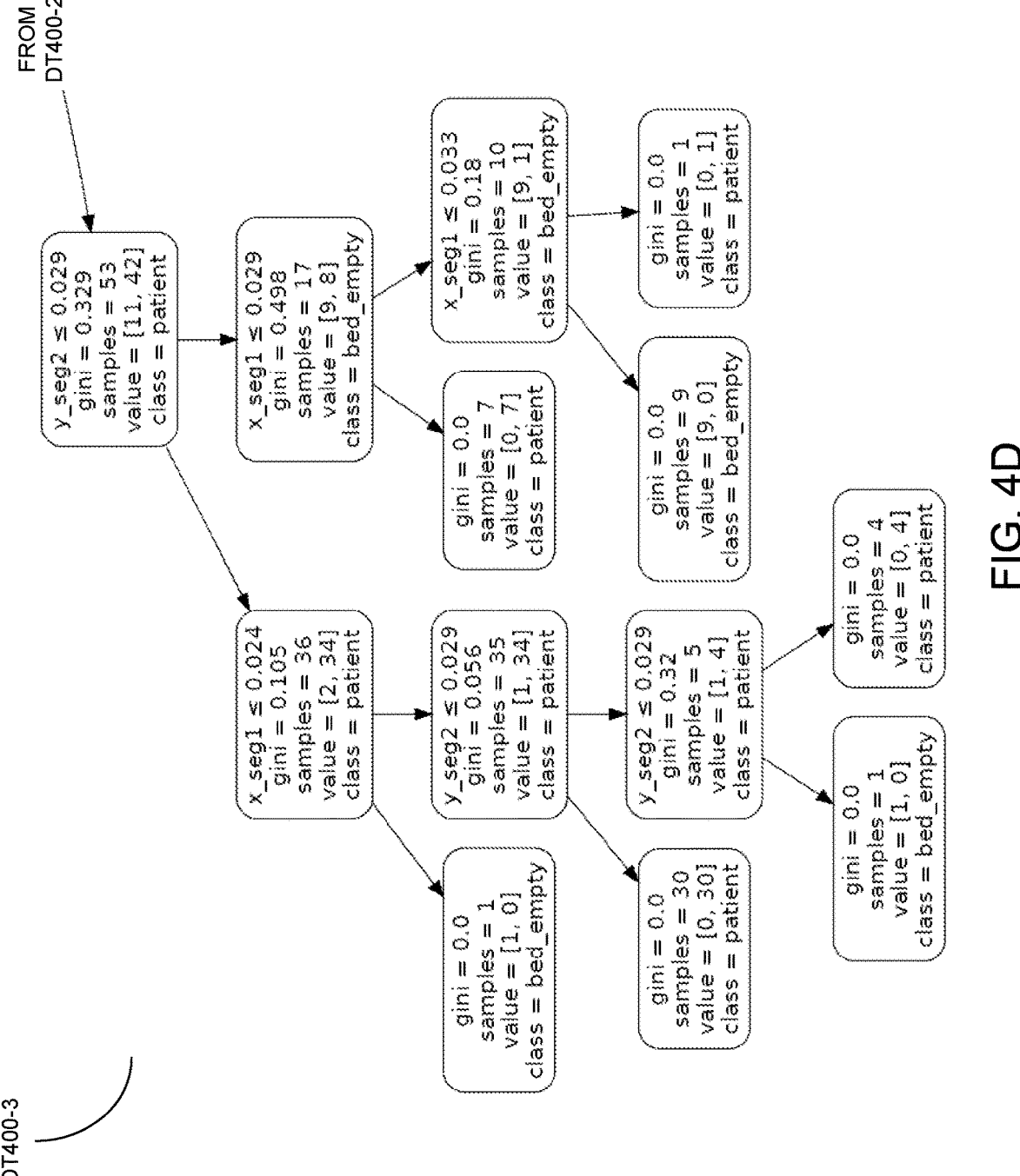
Figure 4E:
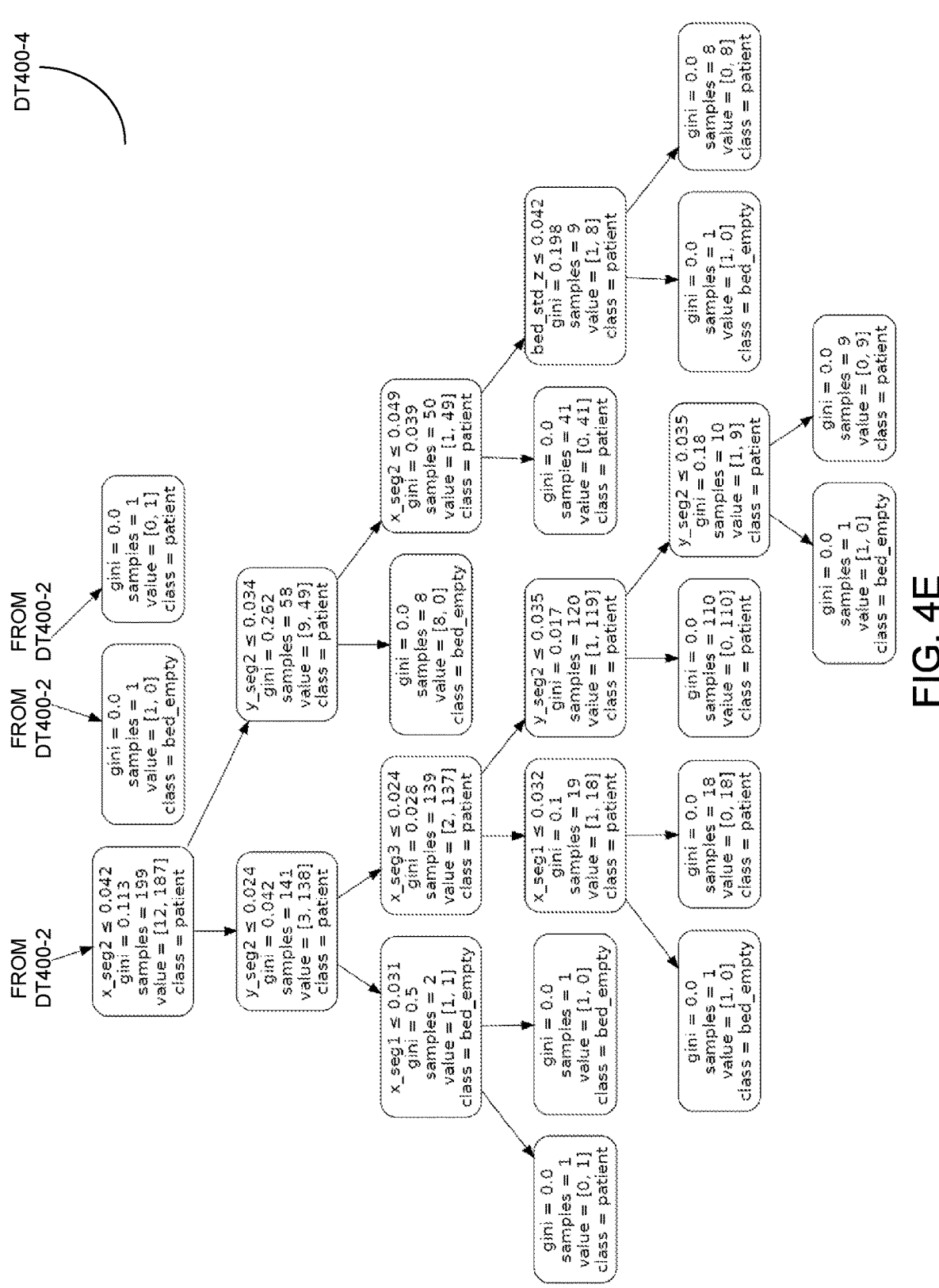

FIG. 4A graphically illustrates an exemplary process of constructing a DT classifier for bed occupancy detection system 100 based a set of 630 training samples and the trained DT classifier 400 with a root node 402 and many levels of sub-nodes and the associated split decisions in accordance with some embodiments described herein. As can be seen in FIG. 4A, root node 402 is constructed based on one of the two extracted Y features and a split value of 0.024. The split condition at root node 402 causes the combined 630 training samples (344 of the NOP class and 286 of the OP class) to split into 210 samples (True samples) to the left branch, and 420 samples (False samples) to the right branch. Each branch continues to split until either Gini=0.0 at sub-node is reached indicating an unoccupied bed, or Gini=1.0 at a sub-node is reached indicating a patient-occupied bed. The computed Gini index for root node 402 is close to but slightly less than 0.5, indicating the split condition at root node 402 causes a maximum possible differentiation/split between the two classes of training samples.

Due to the large size and high complexity of trained DT classifier 400 and for the ease of viewing the DT classifier 400 specificities, trained DT classifier 400 is partitioned into four portions: DT400-1, DT400-2, DT400-3, and DT400-4, and each of the sub-threes is separately illustrated with higher resolution in a set of FIGS. 4B-4E, respectively. Moreover, the original interconnections within trained DT classifier 400 among the four portions are also indicated at their respective boundaries. For example, one branch of the splitting at a second-level sub-node 404 within DT400-1 creates a third-level sub-node 406 within DT400-2.

Making OR Bed Occupancy Inferences by the Trained DT Classifier

Figure 5:
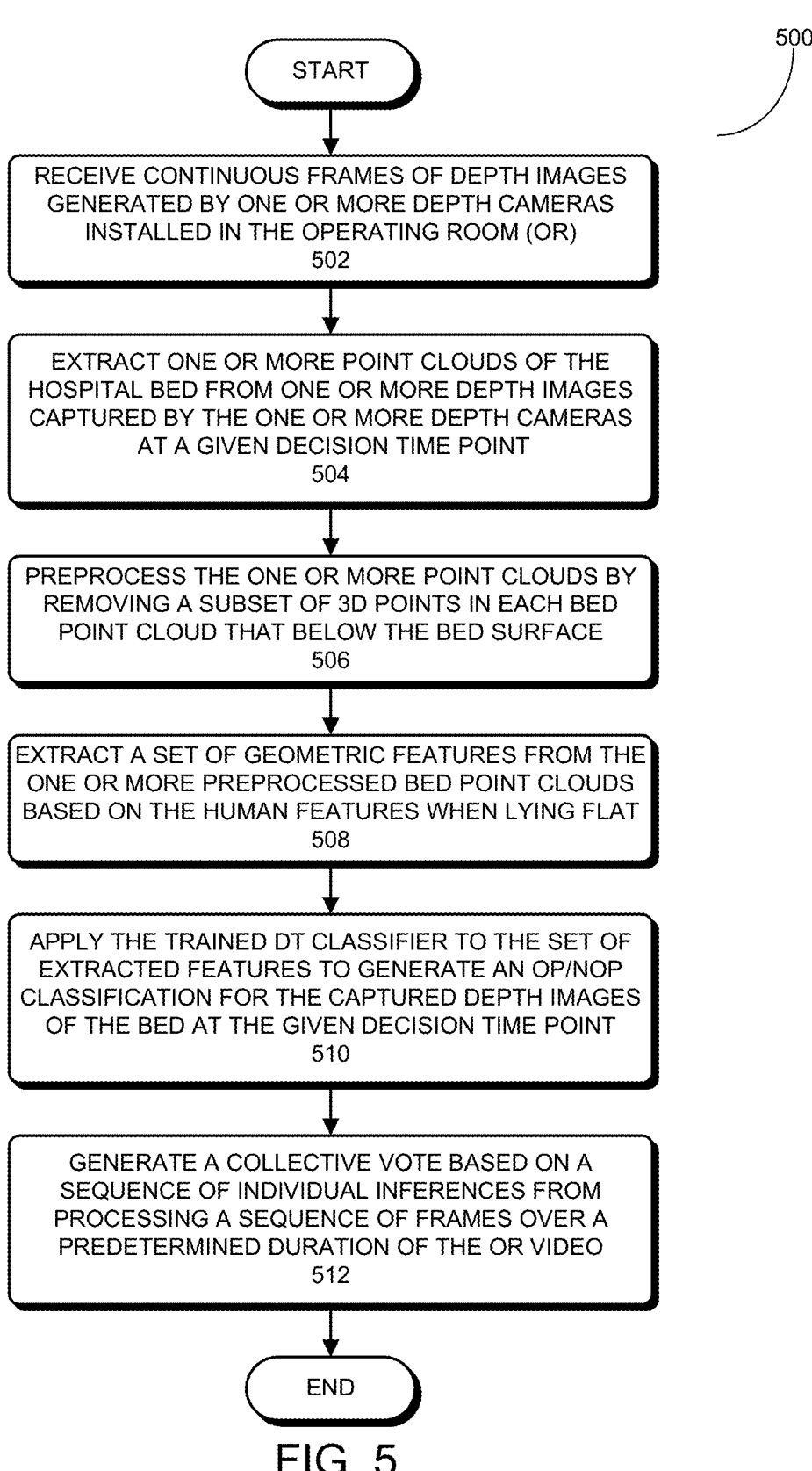
FIG. 5 presents a flowchart illustrating a process for making hospital bed occupancy inferences using the disclosed hospital-bed occupancy detection system in accordance with some embodiments described herein.

FIG. 5 presents a flowchart illustrating an exemplary process 500 for making hospital bed occupancy inferences using the disclosed hospital-bed occupancy detection system in accordance with some embodiments described herein. In one or more embodiments, one or more of the steps in FIG. 5 may be omitted, repeated, and/or performed in a different order. Accordingly, the specific arrangement of steps shown in FIG. 5 should not be construed as limiting the scope of the technique.

Process 500 may begin by receiving continuous frames of depth images generated by one or more depth cameras installed in the OR (step 502). Next, at each given decision time point based on a predetermined time interval, process 500 extracts one or more point clouds of the hospital bed from one or more depth images captured by the one or more depth cameras (step 504). For example, the predetermined time interval for making inferences can be every frame, every 30 seconds, every minute, etc. In some embodiments, the one or more depth images capture the hospital bed from multiple viewing angles, including at least one top-view of the bed and at least one side-view of the bed. Next, process 500 preprocesses the one or more point clouds by removing a subset of 3D points in each bed point cloud that is below the hospital bed surface (step 506). In some embodiments, pre-processing each of the bed point clouds to remove 3D points below the bed surface includes removing those 3D points that have z-values below the computed mean z-value of the given point cloud.

Next, process 500 extracts a set of geometric features from the one or more preprocessed bed point clouds based on the common contour features when a human lying flat on the bed (step 508). In some embodiments, the set of extracted geometric features is the set of six disclosed geometric features based at least on the disclosed X and Y segmentations of each preprocessed point cloud. Next, process 500 applies the trained DT classifier to the set of extracted features, which automatically generates an OP/NOP classification/inference for the captured depth images of the hospital bed at the given decision time point (step 510).

Note that process 500 can continuously process the received continuous sequence of frames using the trained DT classifier while generating individual and continuous inferences for the bed occupancy at a sequence of decision time points, indicating whether the bed is occupied or not occupied by a patient. In some embodiments, instead of responding to and generating a vote for each new classification after processing a given frame captured by the depth camera, process 500 generates a collective decision/vote based on a sequence of individual inferences generated from processing a sequence of frames over a predetermined duration of the OR video (step 512). In some embodiments, the predetermined duration can be 1 minute of the depth camera outputs, but can also be shorter or longer than 1 minute. If recorded at 60 frames-per-second (FPS), then the sequence of frames for 1 minute includes 60 frames. As a specific example, for the sequence of 60 inferences generated for the minute of the OR recording, if 50 inferences are of the OP classification and 10 inferences are of the NOP classification, then the collective decision for the sequence of 60 frames can be an OP inference/decision.

One of the use cases of the disclosed bed occupancy detection system 100 is to detect two types of OR workflow events in real time during a surgical procedure: (1) at the beginning of a surgical procedure when a patient on a hospital bed is being pushed into the OR and (2) at the end of a surgical procedure when a patient on a hospital bed is being pushed out of the OR, and subsequently trigger real-time event warnings/notifications when such events are detected. At the beginning of a surgical procedure, the incorporated 3D object detection and tracking system can be used to detect when a hospital bed is entering the OR. This detection of the hospital bed can then activate the disclosed bed occupancy detection system 100 to determine whether a patient occupies the detected bed entering the OR. If a positive detection is made, a first type of OR event alert can be triggered. Furthermore, toward the end the surgical procedure, the incorporated 3D object detection and tracking system can be used to detect when the hospital bed is exiting the OR. This detection of the hospital bed would again activate the disclosed bed occupancy detection system 100 to determine whether a patient occupies the detected bed exiting the OR. If a positive detection is made, a second type of OR event alert can be triggered.

The two types of real-time OR event alerts can then be used for automated people coordination purposes, e.g., to automatically notify surgical staff that it is time to be in the OR. Note that these two types of events are characterized by the hospital bed being occupied by the patient and are contrasting with an empty hospital bed being pushing into or out of the OR. The disclosed bed occupancy detection system 100 can detect these high priority OR events in real-time by distinguishing a hospital bed being occupied by a real person from an empty hospital bed or any of the above-described FP scenarios of a hospital bed. However, the disclosed bed occupancy detection system 100 can also operate to process the recorded OR depth-camera videos in an offline mode to determine at which times these OR events took place during the surgical procedure. Moreover, the disclosed bed occupancy detection system 100 can be used to perform the occupancy detections under two types of hospital bed OR scenarios: (1) when the hospital bed is in motion; and (2) when the hospital bed is stationary.

The disclosed bed occupancy detection system and technique rely exclusively on depth sensor/camera outputs and the associated point cloud data without the need for the RGB/color information. As a result, the disclosed bed occupancy detection system and technique provide significantly improved privacy protection. Moreover, compared with RGB-image techniques, the disclosed bed occupancy detection system and technique use the geometric features of human body extracted from the point clouds to differentiate from other non-human objects. Such point-cloud-based geometric features remain distinguishable and therefore are not affected when the patient is under a blanket or bed sheet. In contrast, the existing RGB-image or other 2D image detectors will fail under such circumstances.

Note that while we have described the bed occupancy detection system 100 and the associated decision tree classifier 110 in term of a hospital bed used for transporting a patient into and out of the OR, the disclosed bed occupancy detection systems and techniques can be readily extended and applied to a surgical table in the OR where a patient is being operated on during a surgical procedure. As a result, the disclosed bed occupancy detection systems and techniques can be used to determine whether a surgical table is empty or occupied by a patient. Hence, the disclosed bed occupancy detection systems and techniques is not limited to detecting occupancies of hospital beds in the ORs.

Figure 6:
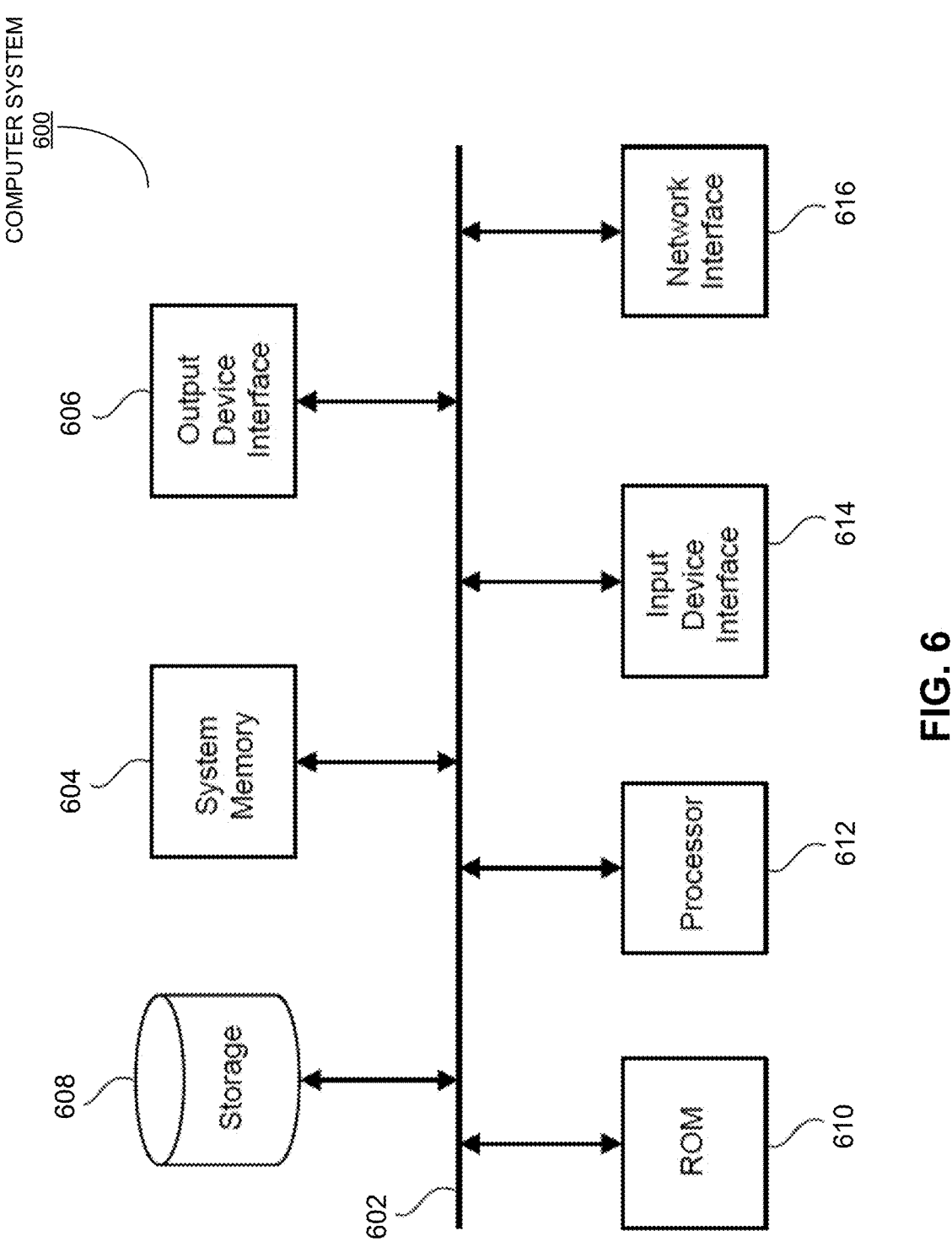
FIG. 6 conceptually illustrates a computer system with which some embodiments of the subject technology can be implemented.

FIG. 6 conceptually illustrates a computer system with which some embodiments of the subject technology can be implemented. Computer system 600 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 600 includes a bus 602, processing unit(s) 612, a system memory 604, a read-only memory (ROM) 610, a permanent storage device 608, an input device interface 614, an output device interface 606, and a network interface 616. In some embodiments, computer system 600 is a part of a robotic surgical system.

Bus 602 collectively represents all system, peripheral, and chipset buses that communicatively connect the numerous internal devices of computer system 600. For instance, bus 602 communicatively connects processing unit(s) 612 with ROM 610, system memory 604, and permanent storage device 608.

From these various memory units, processing unit(s) 612 retrieves instructions to execute and data to process in order to execute various processes described in this patent disclosure, including the point-cloud-based hospital bed occupancy detection processes described in conjunction with FIGS. 1-5. The processing unit(s) 612 can include any type of processor, including but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 612 can be a single processor or a multi-core processor in different implementations.

ROM 610 stores static data and instructions that are needed by processing unit(s) 612 and other modules of the computer system. Permanent storage device 608, on the other hand, is a read-and-write memory device. This device is a non-volatile memory unit that stores instructions and data even when computer system 600 is off. Some implementations of the subject disclosure use a mass-storage device (such as a magnetic or optical disk and its corresponding disk drive) as permanent storage device 608.

Other implementations use a removable storage device (such as a floppy disk, flash drive, and its corresponding disk drive) as permanent storage device 608. Like permanent storage device 608, system memory 604 is a read-and-write memory device. However, unlike storage device 608, system memory 604 is a volatile read-and-write memory, such as a random access memory. System memory 604 stores some of the instructions and data that the processor needs at runtime. In some implementations, various processes described in this patent disclosure, including the point-cloud-based hospital bed occupancy detection processes described in conjunction with FIGS. 1-5, are stored in system memory 604, permanent storage device 608, and/or ROM 610. From these various memory units, processing unit(s) 612 retrieves instructions to execute and data to process in order to execute the processes of some implementations.

Bus 602 also connects to input and output device interfaces 614 and 606. Input device interface 614 enables the user to communicate information to and select commands for the computer system. Input devices used with input device interface 614 include, for example, alphanumeric keyboards and pointing devices (also called "cursor control devices"). Output device interface 606 enables, for example, the display of images generated by computer system 600. Output devices used with output device interface 606 include, for example, printers and display devices, such as cathode ray tubes (CRT) or liquid crystal displays (LCD). Some implementations include devices such as a touch-screen that functions as both input and output devices.

Finally, as shown in FIG. 6, bus 602 also couples computer system 600 to a network (not shown) through a network interface 616. In this manner, the computer can be a part of a network of computers (such as a local area network ("LAN"), a wide area network ("WAN"), an intranet, or a network of networks, such as the Internet. Any or all components of computer system 600 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. The terms "disk" and "disc," as used herein, include compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for determining if a bed inside an operating room (OR) is occupied by a patient, the method comprising:

segmenting a three-dimensional (3D) point cloud of a bed object within a depth image captured in an OR into a plurality of segments in both a length direction and a width direction of the bed object, by i) segmenting the 3D point cloud along a length direction of the bed object into a first plurality of segments being three equal-sized segments, and ii) segmenting the 3D point cloud along a width direction of the bed object into a second plurality of segments; and then extracting a set of geometric features from the plurality of segments; and then applying a binary classifier to the set of geometric features to classify the bed object as either being occupied by a patient or not being occupied by a patient.

2. The computer-implemented method of claim 1, wherein the depth image is captured by a depth camera installed in the OR, and wherein the method further comprises extracting the 3D point cloud from the depth image by projecting each 2D pixel (u, v) and the corresponding distance value d(u, v) in the depth image into a 3D point (x, y, z) in a 3D-coordinate system aligned with the depth camera.

3. The computer-implemented method of claim 1, wherein the second plurality of segments are two equal-sized segments.

4. The computer-implemented method of claim 3, wherein extracting the set of geometric features from the plurality of segments includes:

computing a set of standard deviations of height values using the z-component of a subset of the 3D point cloud associated with each segment of the first plurality of equal-sized segments along the length direction; and computing a set of standard deviations of height values using the z-component of a subset of the 3D point cloud associated with each segment of the second plurality of equal-sized segments along the width direction.

5. The computer-implemented method of claim 4 wherein the patient is lying flat on the bed object, and wherein computing the set of standard deviations of height values using the z-component associated with each segment of the first plurality of segments along the length direction captures unique height distributions in each section of the patient's body in the length direction.

6. The computer-implemented method of claim 4 wherein the patient is lying flat on the bed object, and wherein computing the set of standard deviations of height values using the z-component associated with each segment of the second plurality of segments along the width direction captures a geometrical symmetry along the width direction.

7. The computer-implemented method of claim 1, wherein prior to segmenting the 3D point cloud of the bed object, the method further comprises preprocessing the 3D point cloud by:

computing an average height value of the z-component of the 3D point cloud; and removing a subset of 3D points in the 3D point cloud with the z-component values smaller than the computed average height value.

8. The computer-implemented method of claim 7, wherein extracting the set of geometric features further includes:

computing an overall standard deviation of height values using the z-component of the remaining 3D points in the 3D point cloud after preprocessing the 3D point cloud; and

combining the overall standard deviation as an additional geometric feature with the set of geometric features extracted from the plurality of segments.

9. The computer-implemented method of claim 1, wherein applying the binary classifier to the set of extracted geometric features to classify the bed object includes applying a decision tree classifier to the set of extracted geometric features, which outputs either a positive classification indicating the bed object is occupied by a patient or a negative classification indicating the bed object is not occupied by a patient.

10. The computer-implemented method of claim 9, wherein applying the binary classifier to the set of extracted geometric features to classify the bed object as the negative classification includes identifying and classifying a set of false positives associated with the bed object as the negative classification.

11. The computer-implemented method of claim 10, wherein the set of false positives includes scenarios when the bed object is occupied by various non-human objects including:
one or more boxes;
one or more OR equipments; and
one or more blankets.

12. The computer-implemented method of claim 1, wherein prior to applying the binary classifier to classify the bed object, the method further comprises:
constructing a training dataset from a set of depth-camera videos capturing OR workflow, wherein the training dataset includes a first class of labeled samples of occupied bed scenarios and a second class of samples of non-occupied bed scenarios; and
training the binary classifier using the training dataset.

13. The computer-implemented method of claim 12, wherein the non-occupied bed scenarios include both empty bed scenarios and non-human-object occupied bed scenarios.

14. The computer-implemented method of claim 12, wherein the training dataset includes training samples extracted from depth images of a training bed object captured from multiple viewing angles that include at least a top-view of the training bed object.

15. The computer-implemented method of claim 1, wherein the bed object includes:
a hospital bed used for transporting a patient into and out of the OR; and
a surgical table used to operate a patient during a surgical procedure in the OR.

16. The computer-implemented method of claim 1, wherein applying the binary classifier to the set of geometric features extracted from the 3D point cloud does not require color images of the OR.

17. The computer-implemented method of claim 1, wherein prior to segmenting the 3D point cloud of the bed object, the method further comprises receiving the depth image among a sequence of depth images captured in the OR.

18. An apparatus for determining if a bed inside an operating room (OR) is occupied by a patient, the apparatus comprising:
one or more processors;
a memory coupled to the one or more processors, the memory storing instructions that, when executed by the one or more processors, cause the apparatus to:
segment a three-dimensional (3D) point cloud of a bed object within a depth image captured in an OR into a plurality of segments in both a length direction and a width direction of the bed object, by i) segmenting the 3D point cloud along a length direction of the bed object into a first plurality of segments, and ii) segmenting the 3D point cloud along a width direction of the bed object into a second plurality of segments being two equal-sized segments;
extract a set of geometric features from the plurality of segments; and
apply a binary classifier to the set of geometric features to classify the bed object as either being occupied by a patient or not being occupied by a patient.

19. The apparatus of claim 18, wherein the memory further stores instructions that, when executed by the one or more processors, cause the apparatus to preprocess the 3D point cloud prior to segmenting the 3D point cloud by:
computing an average height value of the z-component of the 3D point cloud; and
removing a subset of 3D points in the 3D point cloud with the z-component values smaller than the computed average height value.

20. The apparatus of claim 18, wherein the memory further stores instructions that, when executed by the one or more processors, cause the apparatus to receive the depth image among a sequence of depth images captured in the OR prior to segmenting the 3D point cloud of the bed object.

21. A system for determining if a bed inside an operating room (OR) is occupied by a patient, the system comprising:
one or more depth cameras installed in the OR;
one or more processors coupled to the one or more depth cameras; and
a memory coupled to the one or more processors, the memory storing instructions that, when executed by the one or more processors, cause the system to:
segment a three-dimensional (3D) point cloud of a bed object within a depth image captured in an OR into a plurality of segments in both a length direction and a width direction of the bed object;
extract a set of geometric features from the plurality of segments; and
apply a binary classifier to the set of geometric features to classify the bed object as either being occupied by a patient or not being occupied by a patient, wherein the binary classifier comprises a machine learning model trained using a training dataset constructed from a set of depth-camera videos that capture operating room workflow, and the training dataset includes a first class of labeled samples of occupied bed scenarios and a second class of labeled samples of non-occupied bed scenarios, wherein the non-occupied bed scenarios include both empty bed scenarios and non-human-object occupied bed scenarios.

22. The system of claim 21, wherein the one or more depth cameras include at least two depth cameras which are installed in the OR to capture depth images of the bed object from multiple viewing angles that include at least a top-view angle.

23. The system of claim 21, wherein the memory further stores instructions that, when executed by the one or more processors, cause the system to receive the depth image among one or more sequences of depth images captured by the one or more depth cameras prior to segmenting the 3D point cloud of the bed object.

* * * * *